United States Patent
Ulmer et al.

(10) Patent No.: US 10,682,226 B2
(45) Date of Patent: Jun. 16, 2020

(54) HEART VALVE PROSTHESIS (71) Applicant: Biotronik AG, Buelach (CH)

(72) Inventors: Jens Ulmer, Kuesnacht (CH); Nicolas Degen, Beringen (CH)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 15/480,974

(22) Filed: Apr. 6, 2017

(65) Prior Publication Data
US 2017/0290659 A1 Oct. 12, 2017

(30) Foreign Application Priority Data
Apr. 11, 2016 (DE) .................. 10 2016 106 575

(51) Int. Cl.
*A61F 2/24* (2006.01)
(52) U.S. Cl.
CPC .... *A61F 2/2418* (2013.01); *A61F 2220/0008* (2013.01); *A61F 2220/0083* (2013.01); *A61F 2230/0034* (2013.01); *A61F 2250/0036* (2013.01)

(58) Field of Classification Search
CPC ........ A61F 2/2418; A61F 2/2409; A61F 2/24; A61F 2/2475
See application file for complete search history.

(56) References Cited

U.S. PATENT DOCUMENTS

| | | | | |
|---|---|---|---|---|
| 8,597,349 B2 * | 12/2013 | Alkhatib | ............... | A61F 2/2418 623/1.26 |
| 9,232,997 B2 * | 1/2016 | Sugimoto | ............. | A61L 31/022 |
| 2007/0162107 A1 * | 7/2007 | Haug | .................... | A61F 2/2418 623/1.26 |
| 2010/0249911 A1 * | 9/2010 | Alkhatib | ............... | A61F 2/2418 623/1.26 |
| 2010/0331972 A1 * | 12/2010 | Pintor | .................. | A61F 2/2409 623/2.11 |
| 2011/0295363 A1 * | 12/2011 | Girard | .................. | A61F 2/2412 623/1.26 |
| 2011/0319989 A1 * | 12/2011 | Lane | ..................... | A61F 2/2418 623/2.11 |
| 2012/0078347 A1 * | 3/2012 | Braido | ................. | A61F 2/2418 623/1.26 |

(Continued)

FOREIGN PATENT DOCUMENTS

| WO | 2009/061389 A2 | 5/2009 |
|---|---|---|
| WO | 2011/137531 A1 | 11/2011 |
| WO | 2015/0175524 A1 | 11/2015 |

OTHER PUBLICATIONS

EP17164727.4 European Search Report dated Oct. 5, 2017.
DE2016106575.7 German Search Report dated Jan. 27, 2017.

*Primary Examiner* — Alvin J Stewart
(74) *Attorney, Agent, or Firm* — Wagenknecht IP Law Group PC (57) ABSTRACT A heart valve prosthesis (1), including: a stent framework (2), which can be transferred from a collapsed state into an expanded state, in which the stent framework (2) extends along an axis (A'), wherein the stent framework (2) has a plurality of struts (20, 24), which form a plurality of cells (21a, 21b, 25) connected to one another; and a heart valve (3), which is fixed to the stent framework (2). In accordance with the invention, the thickness (d') of the struts varies in the peripheral direction (U) of the expanded stent framework (2).

18 Claims, 6 Drawing Sheets

FIG. 2

(56) References Cited

U.S. PATENT DOCUMENTS

| | | | |
|---|---|---|---|
| 2013/0211508 A1* | 8/2013 | Lane | A61F 2/2403 623/2.11 |
| 2013/0331933 A1* | 12/2013 | Alkhatib | A61F 2/2418 623/2.37 |
| 2014/0012371 A1* | 1/2014 | Li | A61F 2/2415 623/2.12 |
| 2014/0222142 A1* | 8/2014 | Kovalsky | A61F 2/2418 623/2.17 |
| 2015/0127093 A1* | 5/2015 | Hosmer | A61F 2/2418 623/2.11 |
| 2015/0173898 A1* | 6/2015 | Drasler | A61F 2/2418 623/2.18 |
| 2016/0213465 A1* | 7/2016 | Girard | A61F 2/2418 |
| 2016/0331525 A1* | 11/2016 | Straubinger | A61F 2/07 |
| 2016/0367359 A1* | 12/2016 | Scorsin | A61F 2/2412 |
| 2016/0367360 A1* | 12/2016 | Cartledge | A61F 2/2418 |
| 2016/0374801 A1* | 12/2016 | Jimenez | A61F 2/2418 623/2.18 |
| 2017/0189180 A1* | 7/2017 | Alkhatib | A61F 2/2418 |
| 2017/0209264 A1* | 7/2017 | Chau | A61F 2/2418 |
| 2017/0231760 A1* | 8/2017 | Lane | A61F 2/2418 623/2.11 |
| 2017/0281338 A1* | 10/2017 | Quill | A61F 2/2409 |
| 2017/0333187 A1* | 11/2017 | Hariton | A61F 2/2436 |
| 2017/0348100 A1* | 12/2017 | Lane | A61F 2/2409 |
| 2017/0367822 A1* | 12/2017 | Naor | A61F 2/2418 |
| 2018/0000580 A1* | 1/2018 | Wallace | A61F 2/2418 |
| 2018/0008405 A1* | 1/2018 | Girard | A61F 2/2412 |
| 2018/0014930 A1* | 1/2018 | Hariton | A61F 2/2418 |
| 2018/0021127 A1* | 1/2018 | Yohanan | A61F 2/2433 |
| 2018/0042555 A1* | 2/2018 | Braido | A61B 5/6862 |
| 2018/0055629 A1* | 3/2018 | Oba | A61F 2/2409 |

\* cited by examiner

HEART VALVE PROSTHESIS

CROSS REFERENCE TO RELATED APPLICATIONS

This application claims benefit of priority to German patent application no. DE 10 2016 106 575.7, filed Apr. 11, 2016; the entire content of which is herein incorporated by reference in its entirety.

TECHNICAL FIELD

The invention relates to a heart valve prosthesis, in particular for the transcutaneous replacement of a heart valve, preferably a mitral valve, secured to an expandable stent framework that varies in thickness in a peripheral direction.

BACKGROUND OF THE INVENTION

Heart valve prostheses as described herein generally have a stent framework, which can be transferred from a collapsed state into an expanded state and has a plurality of struts, which form a plurality of cells connected to one another, and also a heart valve (in particular made of a biological tissue), which is fixed to the stent framework.

When implanting artificial heart valves, in particular a mitral valve, it is necessary for the correct and durable functioning of the artificial heart valve, to adapt the valve to the anatomical environment in the region of the natural heart valve (annulus). For example, it is necessary to form the valve asymmetrically in terms of its radial geometry. Here, the D-shaped annulus geometry of the native valve should be taken into consideration.

On this basis, the object of the present invention is to provide a heart valve prosthesis which enables an adaptation of this type.

SUMMARY OF THE INVENTION

This object is achieved by a heart valve prosthesis secured to an expandable stent framework that varies in thickness in the peripheral direction. Further advantageous embodiments of the invention are specified and described hereinafter.

In particular, a provision is made in accordance with the invention so that the thickness of the struts varies in the peripheral direction of the stent framework.

Here, the stent framework in the expanded state preferably extends along an axis, along which the blood of the receiver of the prosthesis flows through an interior of the stent framework defined or surrounded by the stent framework when the prosthesis has been implanted as intended, wherein the stent framework runs around in the peripheral direction of the stent framework, which runs around perpendicularly to the aforesaid axis.

In accordance with a particularly preferred embodiment of the invention, provision is made so that the heart valve prosthesis is configured to take over the function of a native heart valve, wherein the heart valve of the heart valve prosthesis is a mitral valve.

In accordance with a particularly preferred embodiment of the invention, provision is also made so that the thickness of the struts varies in the peripheral direction, in such a way that the stent framework in the expanded and implanted state has a peripheral cross-sectional contour, which is adapted to the mitral valve annulus of the mitral valve that is to be replaced, wherein the cross-sectional contour is in particular D-shaped.

In other words, in accordance with one embodiment of the invention, the cross-sectional contour in the implanted state has a flattened first portion and an arcuate second portion connected thereto, wherein the flattened portion extends from the region of the left fibrous trigone to the region of the right fibrous trigone, based on the expanded and implanted state of the stent framework.

In accordance with a preferred embodiment of the invention, provision is also made so that the geometry of the cells of the stent framework varies in the peripheral direction, in such a way that the stent framework in the expanded and implanted state has a peripheral cross-sectional contour which is adapted to the mitral valve annulus of the mitral valve that is to be replaced, wherein said cross-sectional contour is in particular D-shaped.

Within the scope of this application, a distinction is preferably made between three fundamental states for the stent framework: the compressed state, the expanded state, and the implanted state (also referred to often hereinafter as the "expanded and implanted state"). The expanded state is the normal state of the stent framework. This free, expanded state is adopted by the stent framework in free space without any influence of external forces. In the compressed state, the stent framework is compressed in its radial extent by the influence of external forces. It is in this state that the prosthesis is usually introduced into the body, in particular by means of an insertion catheter, and is transported to the site of implantation. With implantation of the prosthesis, the stent framework re-adopts its expanded and now implanted state. The implanted state differs from the freely expanded state in that the stent framework is disposed in the outer environment of the site of implantation, which acts accordingly on the expanded stent framework.

The stent framework of this preferred embodiment would adopt a circular cross-section in its pure expanded form. However, the variation according to the invention of the thickness of the struts of the stent framework allows the prosthesis or the stent framework to adapt to the natural cross-section of the mitral valve annulus and to adopt a cross-section as described above.

In accordance with a particularly preferred embodiment of the invention, provision is made so that the stent framework has first struts which come to lie in the region of the left fibrous trigone and in the region of the right fibrosis trigone, based on the expanded and implanted state of the stent framework, wherein these first struts have a smaller thickness than the second struts of the stent framework, which come to lie on the mitral valve annulus further away from the left fibrous trigone and the right fibrous trigone.

According to this embodiment a cross-sectional contour is achieved, which consists essentially of a flattened first portion and an arcuate second portion connected thereto, wherein the flattened portion extends from the left fibrous trigone to the right fibrous trigone, based on the expanded and implanted state of the stent framework. If the thinner first struts are positioned at the trigones, the stent framework could more easily bend or kink at these positions. Thereby a D-shaped cross-sectional contour is achieved, which corresponds to the natural geometry at the mitral annulus. It is not necessary to pre-set a D-shaped cross-sectional contour in the expanded shape, which leads to a much easier manufacturing process. A D-shaped cross-sectional contour is naturally achieved in the implanted state of the stent framework.

In accordance with a particularly preferred embodiment of the invention, provision is made so that the stent framework has first struts which come to lie in the region of the left fibrous trigone and in the region of the right fibrous trigone, based on the expanded and implanted state of the stent framework, wherein the stent framework has a stent structure that is modified in these regions and which consequently leads to a local weakening of the radial force of the stent framework.

In accordance with a particularly preferred embodiment of the invention, provision is made so that the stent framework in the region of the left fibrous trigone and in the region of the right fibrous trigone has an open cell structure, in which two or more cells are not connected to one another.

In accordance with a particularly preferred embodiment of the invention, provision is made so that the stent framework in the region of the left fibrous trigone and in the region of the right fibrous trigone has a modified cell geometry, in which the size and number of the cells varies in these regions.

In accordance with a preferred embodiment of the invention, provision is made so that the first struts have a thickness which lies in the region of 0.5 times to 0.9 times the thickness of the second struts, wherein the thickness of the first struts is preferably 0.7 times to 0.9 times, in particular 0.8 times the thickness of the second struts.

The struts of the stent framework in accordance with an embodiment of the invention are preferably integrally connected to one another or integrally formed on one another via connection regions.

In accordance with a preferred embodiment of the invention, provision is also made so that the first struts form two cells of the stent framework, which are arranged adjacently or above one another in the direction of the axis of the stent framework and are connected to one another via a connection region, wherein said two cells come to lie in the region of the left fibrous trigone, based on the expanded and implanted state of the stent framework.

In accordance with a preferred embodiment of the invention, provision is also made so that the connection region has a first and a second edge portion, wherein the two edge portions lie opposite one another in the peripheral direction when a stent framework is expanded, wherein a recess is formed in each edge portion, and wherein the two recesses are arranged offset relative to one another in the direction of said axis of the stent framework.

In accordance with a preferred embodiment of the invention, provision is made similarly so that the first struts form two further cells of the stent framework, which are arranged adjacently or above one another in the direction of said axis and are connected to one another via a further connection region, wherein said two further cells come to lie in the region of the right fibrous trigone, based on the expanded and implanted stated the stent framework.

In accordance with a preferred embodiment of the invention, provision is also made so that the further connection region has a first and a second edge portion, wherein the two edge portions lie opposite one another in the peripheral direction, wherein a recess is formed in each edge portion, and wherein the two recesses are arranged offset relative to one another in the direction of the axis.

The smaller thicknesses of the struts in the region of the left and right trigone and also the above-described thinning of the connection regions of the thinner struts or cells advantageously enable or promote a deformation of the expanded stent framework, wherein the stent framework has the geometry or cross-sectional contour adapted to the mitral valve annulus (in particular D-shaped cross-sectional contour).

In accordance with a preferred embodiment of the invention, provision is also made so that the stent framework has a peripheral first edge region, which surrounds an inflow tract of the heart valve prosthesis, via which blood can flow into the heart valve prosthesis, and also an opposite peripheral second edge region, which defines an outflow tract of the heart valve prosthesis, via which blood can flow out from the heart valve prosthesis.

In accordance with a preferred embodiment of the invention, provision is also made so that the stent framework at the outflow tract has loops for anchoring the heart valve prosthesis to the cusps of the native mitral valve.

In accordance with a preferred embodiment of the invention, two loops are preferably provided in this respect, which are configured to anchor the heart valve prosthesis to the anterior cusp of the native mitral valve.

Here, provision is preferably made so that these two loops run in opposite directions starting from the stent framework, wherein each loop runs in the direction of an assigned trigone of the native mitral valve.

In accordance with a further embodiment of the invention, a further loop (in particular just one) is preferably provided, which is configured to anchor the heart valve prosthesis to the posterior cusp of the native mitral valve, wherein the further loop is shorter in its extension direction than the two loops for the anterior cusp. The length of this further loop is preferably 0.7 to 0.8 times, preferably 0.75 times the length of the two other loops.

In accordance with a preferred embodiment of the invention, provision is also made so that the stent framework has cells for anchoring the heart valve prosthesis to the outflow tract, which cells are curved outwardly.

In accordance with a preferred embodiment of the invention, provision is also made so that the stent framework has shortened cells on a peripheral edge of an inflow tract of the stent framework, the length of said cells in the direction of said axis of the (expanded) stent framework being shorter than the length of cells of the stent framework that are adjacent in the peripheral direction, wherein the shortened cells are configured to come to lie in the region of the aortic peak of the native mitral valve in the expanded and implanted state of the stent framework.

In accordance with a preferred embodiment of the invention, provision is also made so that the heart valve prosthesis is configured to be implanted minimally invasively by means of a catheter.

In accordance with a preferred embodiment of the invention, provision is also made so that the stent framework is expandable (example by means of a balloon), preferably is self-expanding. In the latter case, the stent framework deploys automatically as soon as it is released by the catheter used for implantation, which transports the stent framework in the compressed state to the site of implantation.

DESCRIPTION OF THE DRAWINGS

Further features and advantages of the invention will be explained in the description of the drawings of exemplary embodiments of the invention, which is provided with reference to the drawings as follows.

DETAILED DESCRIPTION

Figure 1:
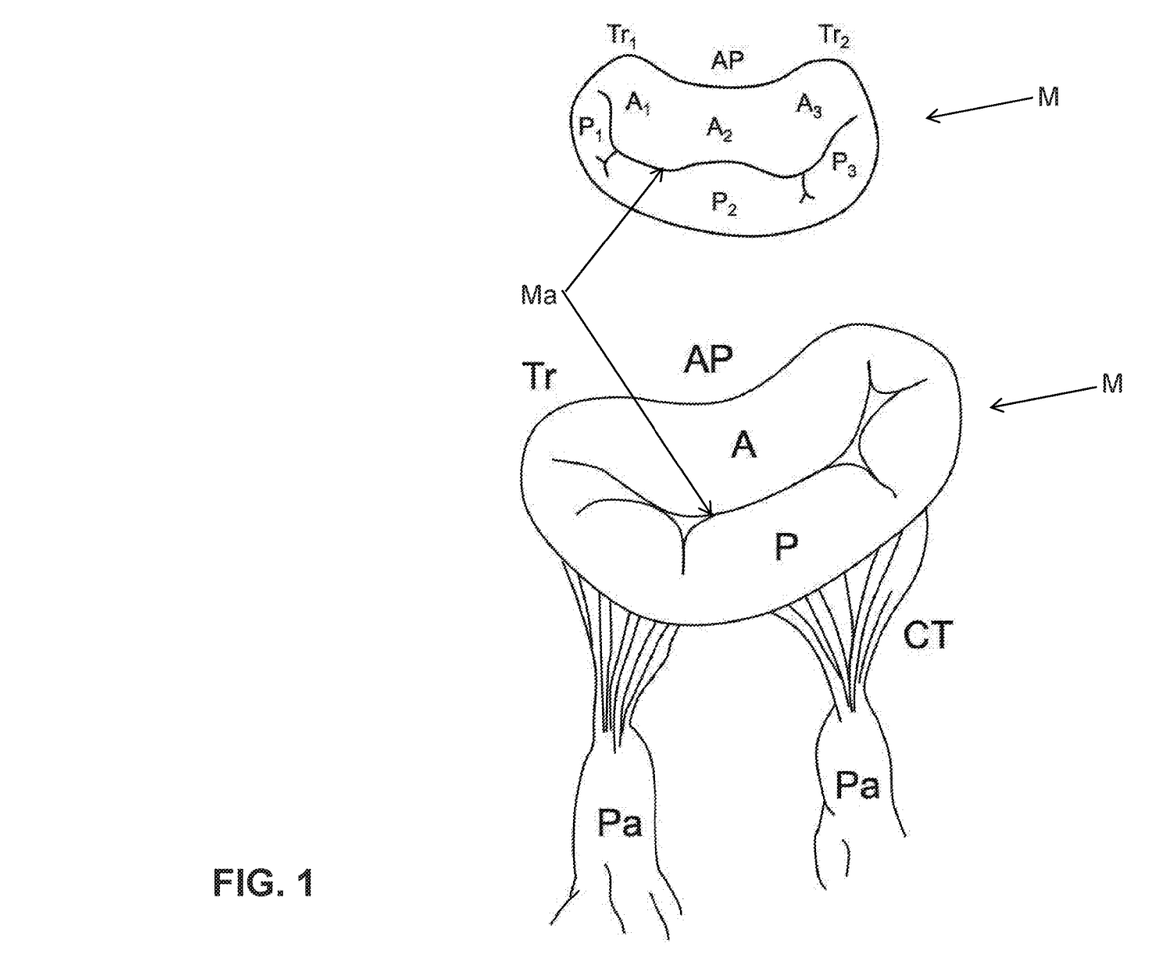
FIG. 1 shows schematic views of a mitral valve.

FIG. 1 shows views of a mitral valve M. The heart valve prosthesis 1 according to the invention is in particular configured to replace a faulty valve M of this type, wherein the prosthesis is displaced laterally by a stent framework 2 of the heart valve prosthesis. The mitral valve annulus Ma forming accordingly has a D-shaped geometry, wherein the stent framework 2 obtains the geometry in the region of the annulus Ma as a result of the provision of struts 20, which in particular are thinner. More specifically, A1 to A3 denote the portions of the anterior valve cusp A, whereas P1 to P3 denote the portions of the posterior valve cusp P. Furthermore, the aortic peak AP and also the left and right fibrous trigone Tr1, Tr2 are shown.

Figure 2:
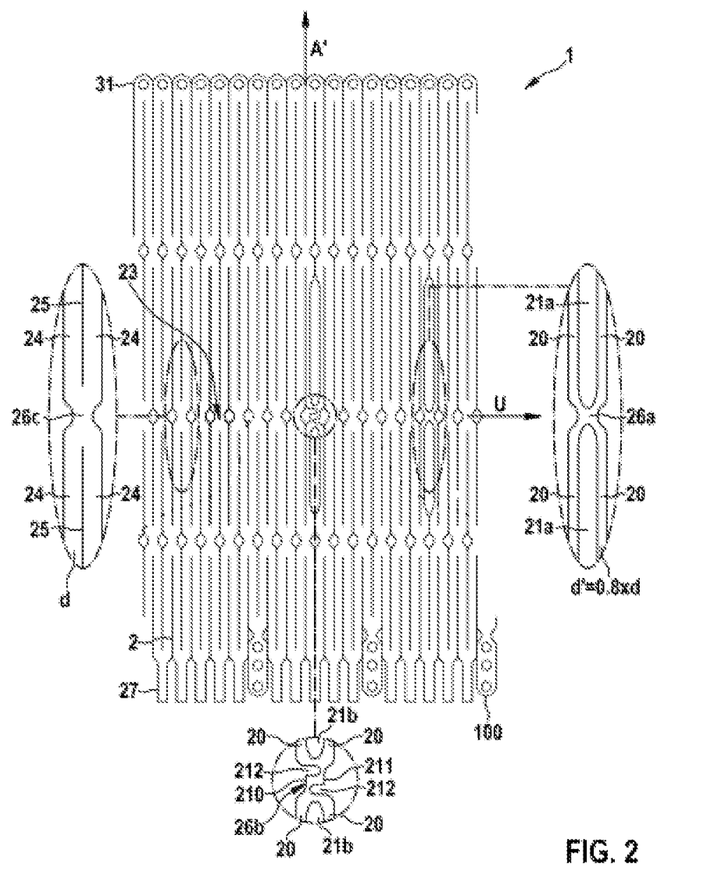
FIG. 2 shows a stent framework of a heart valve prosthesis according to the invention in a state spread out flat.

A cut view of a stent framework 2 according to the invention for the structure of a mitral valve prosthesis 1 is illustrated in FIG. 2. The stent framework 2 has three anchors 100 for the fastening of the commissures of the artificial valve cusps, which are not illustrated here, and also preferably a total of 18 cells 21a, 21b, 25 running around radially, wherein the lower part of the stent cells 21a, 21b, 25 can be provided with extensions, to which additional retaining loops 28, 29 (for example see FIGS. 3 and 4) can be attached. On the whole, the stent cells 21a (or 21b, 25) in this embodiment can be arranged above one another in particular in four rows, and can thus form the stent framework 2 as a whole. What are decisive for obtaining a D-shaped geometry, as mentioned at the outset, are struts 20, 24 of different thickness (d' vs d), which after implantation come to lie in the region of the trigones Tr1, Tr2 (see also FIG. 1), at each of which a region of greatest bend of the cross-sectional contour 23 of the expanded stent framework 2 is present (in the implanted and expanded state the left vertical edge of the cut form is connected to the right edge of the cut form, such that a stent framework 2 is formed accordingly, which extends along a central axis A' and runs around transversely thereto in a peripheral direction U, wherein the stent framework 2 (based on the axis A') forms an inflow tract 31 and an outflow tract 27 at the upper and lower ends respectively).

In order to achieve a suitable curvature of the stent framework 2, the stent thickness d' of the first stent 20 can be 0.8*d compared to the second stent 24 for example, wherein d specifies the thickness of the struts 24 in all other regions (away from the trigones Tr1, Tr2).

In addition to the thinner stent struts 20, the connection regions 26 of the individual (thinner) stent cells 21 are flexible. This makes it possible for the stent geometry to better follow the natural mitral geometry and thus anchor the artificial heart valve better in the annulus Ma.

For this purpose, provision is preferably made for example so that the corresponding connection region 26b of the thinner strut 20 has a first and a second edge portion 210, 211, wherein the two edge portions 210, 211 lie opposite one another in the peripheral direction U of the stent framework 2, wherein a recess is formed in each edge portion 210, 211, wherein the two recesses 212 are arranged offset relative to one another in the direction of the axis A' of the stent framework 2.

Figure 3:
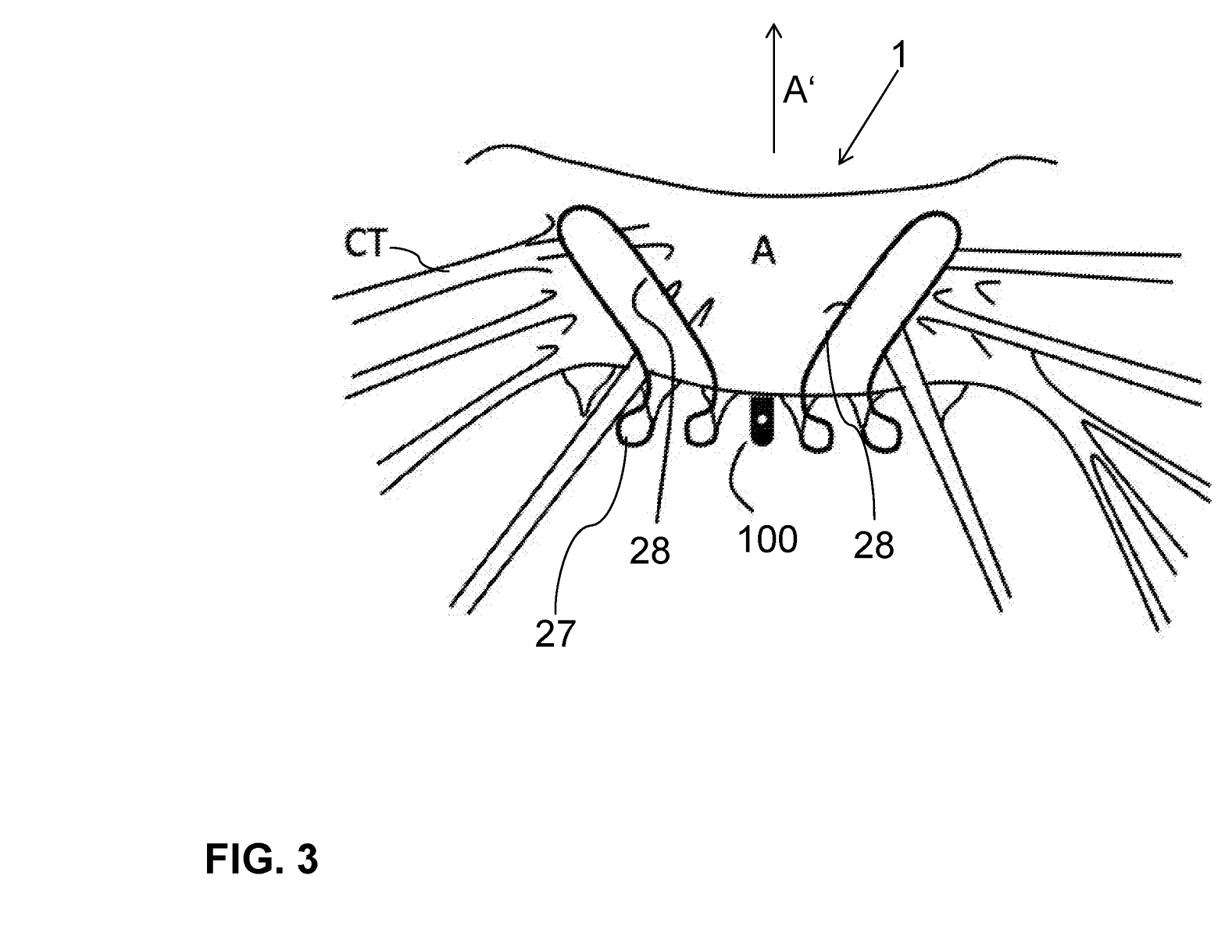
FIG. 3 shows a schematic illustration of a heart valve prosthesis according to the invention in an implanted state.
Figure 4:
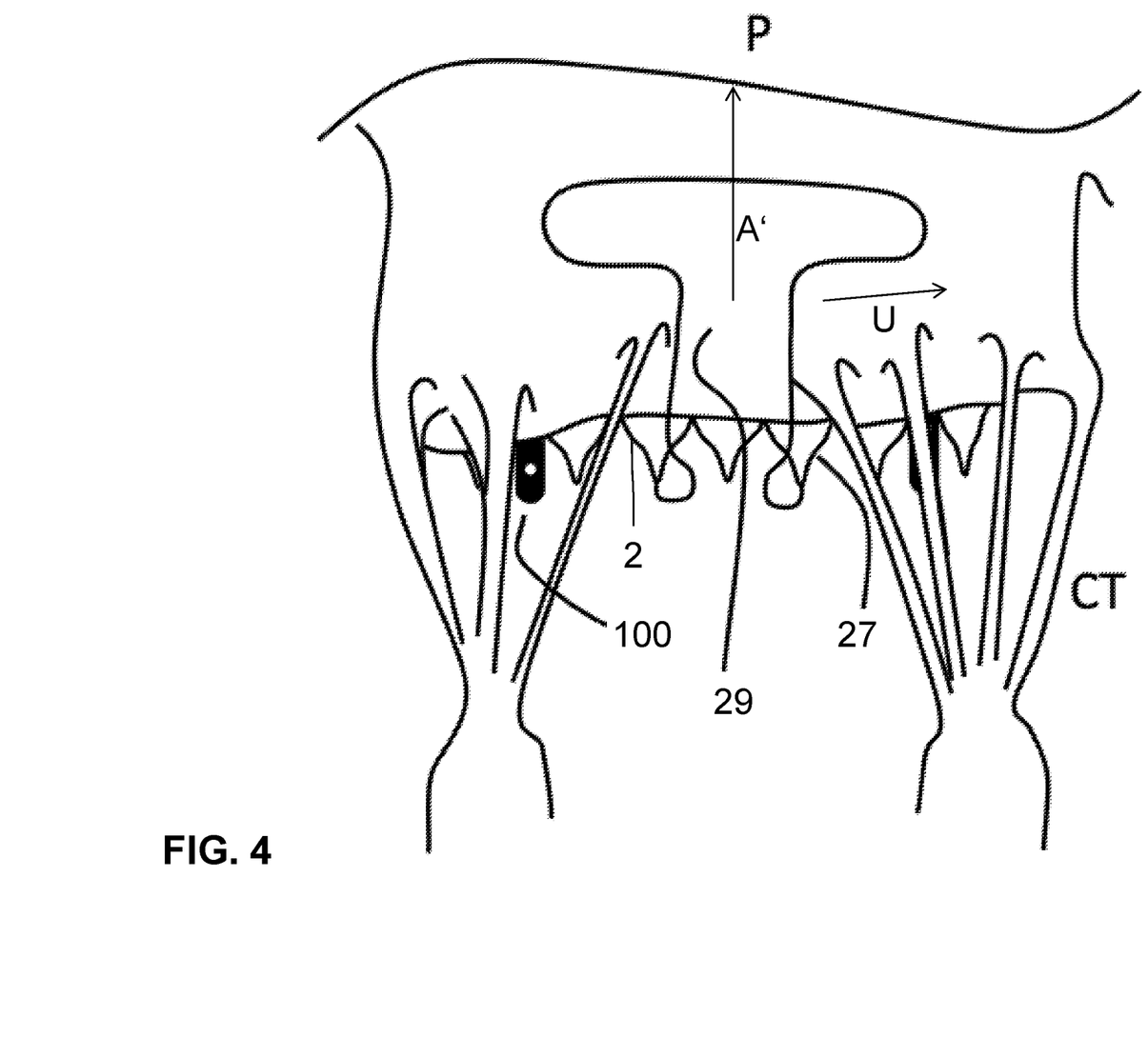
FIG. 4 shows a further schematic illustration of a heart valve prosthesis according to the invention in an implanted state.

For the fixing of the valve 1, loop structures 28 are also preferably attached to the outflow tract 27. Here, two anterior loops 28, for example according to FIG. 3, are attached for the fixing of the anterior cusp A. Here, the loops 28 run from the commissure mounting 100 in the direction of the trigones Tr1, Tr2 so as to be able to be supported there. These loops 28 running at an incline are intended in particular to reduce a hooking with the chordae tendineae CT during implantation. Just one posterior loop 29 is provided in the region of the posterior cusp P (see FIG. 4). This is preferably formed such that it covers the greatest possible area of the cusp P in the distal loop region, without becoming hooked with the chordae tendineae CT during the positioning of the loop 29. Furthermore, the posterior loop 29 is preferably shortened and corresponds in this example approximately to 0.75 times the length of the anterior loop 28.

Figure 5:
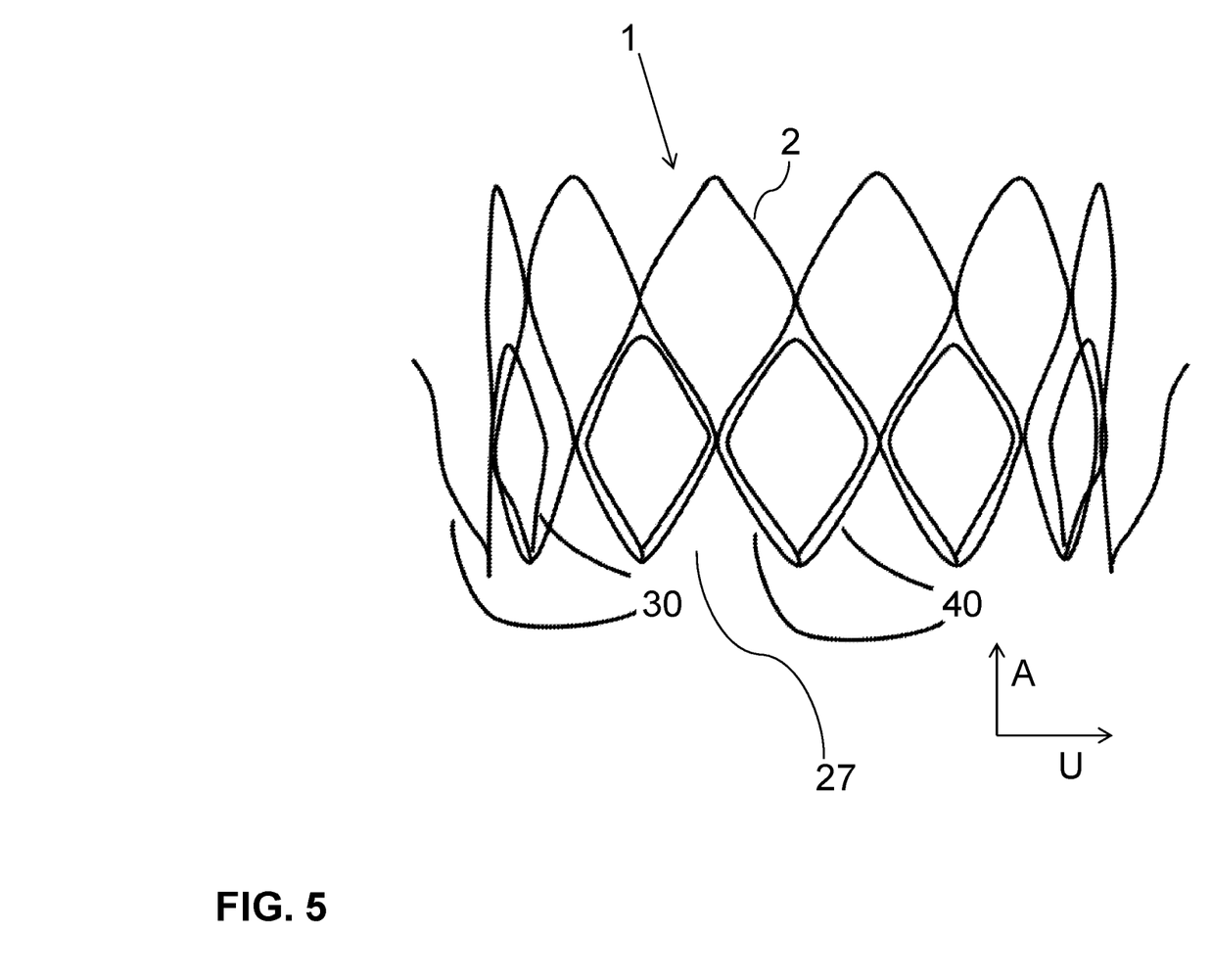
FIG. 5 shows a schematic view of a heart valve prosthesis according to the invention.

What is important for the fixing of the artificial mitral valve 1 is the anchoring with the native cusps (denoted in FIG. 1 by A for anterior cusp and by P for posterior cusp). This can be provided generally by use of large loops (see also FIGS. 3 and 4), which are attached in the outflow tract 27 of the heart valve 1. It is also possible according to FIG. 5 to design the cell geometry such that part 30 of the cell-forming struts 40 can be curved outwardly. The remaining part of the struts 40 then forms the respective cell. It is thus possible to provide an additional anchoring mechanism in the outflow tract 27 of the stent framework 2, which anchoring mechanism protects the artificial valve 1 against a possible dislocation.

Figure 6:
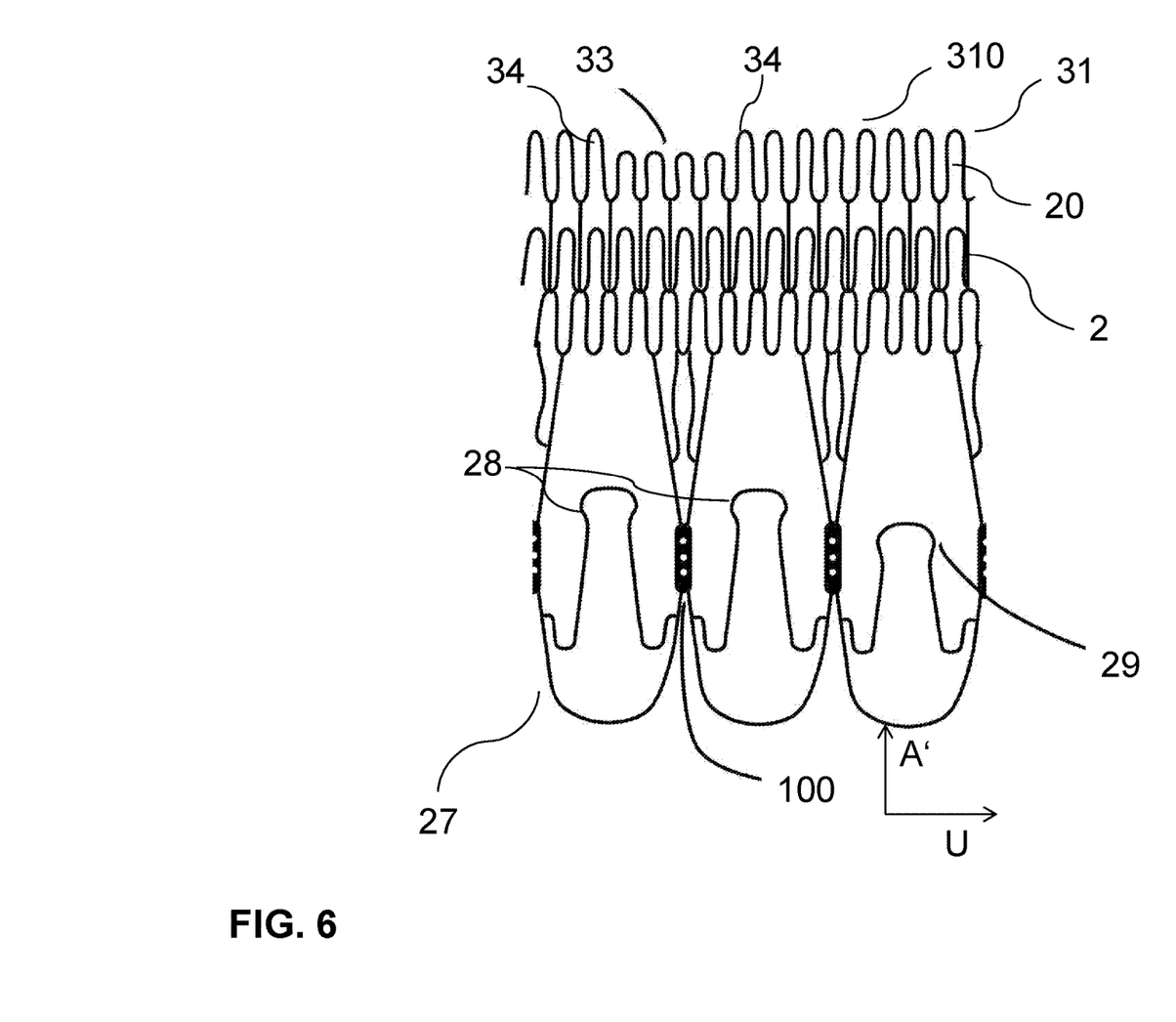
FIG. 6 shows a schematic view of a further stent framework of a heart valve prosthesis according to the invention in a state spread out flat.

A further cut view of a stent framework 2 is shown in FIG. 6, the stent framework having been adapted to the asymmetrical conditions in the region of the mitral annulus (for example by use of the above-described thinner struts 20). The cells 33 are also shortened at the edge 310 of the inflow tract 31 in the region of the aortic peak AP (see FIG. 1) compared to the adjacent cells 34 on either side. Furthermore, the integrated retaining loops 28, 29 again have a different length in the direction of the axis A'. The retaining posterior loop 29 of the posterior cusp P is thus shorter than the two retaining anterior loops 28 of the anterior cusp A. The posterior loop 29 is for example 0.75 times as long here as the corresponding anterior loop 28. Here, it should be noted that an asymmetric D-shape can be impressed on the stent framework 2 in FIG. 4, also with heatsetting. In contrast thereto, the stent framework 2 in FIG. 2 can have a radially symmetrical starting form in the pure expanded state, wherein it can adapt to the D-shape of the natural mitral annulus M on account of the different mechanical properties of the stent framework 2 (caused by the struts 20, 24 of different thickness or the connection regions 26a, 26b, 26c).

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A heart valve prosthesis, comprising:
   a stent framework that extends along an axis and which can be transferred from a collapsed state into an expanded state that when implanted has a D-shaped cross-sectional contour comprising a flattened portion that extends from a region of a left fibrous trigone to a region of a right fibrous trigone and an arcuate portion connected thereto, wherein the stent framework has a plurality of struts, which form a plurality of cells connected to one another, and a heart valve, which is secured to the stent framework, characterized in that first struts configured to lie in the region of a left fibrous trigone and in the region of the right fibrous trigone have a smaller thickness than second struts of the stent framework configured to lie on a mitral valve annulus, wherein the first struts provide opposing ends of the flattened portion when in the implanted and expanded state.

2. The heart valve prosthesis according to claim 1, characterized in that the heart valve prosthesis is configured to take on a function of a native mitral valve, wherein the heart valve of the heart valve prosthesis is a mitral valve.

3. The heart valve prosthesis according to claim 1, characterized in that the thicknesses of the struts vary in the peripheral direction, in such a way that the stent framework in the expanded and implanted state has a peripheral cross-sectional contour which is adapted to the mitral valve annulus of the mitral valve that is to be replaced.

4. The heart valve prosthesis according to claim 1, characterized in that the first struts have a thickness which is 0.5 times to 0.9 times the thickness of the second struts.

5. The heart valve prosthesis according to claim 1, characterized in that the first struts form two cells of the stent framework, which are arranged adjacently in a direction of the axis and are connected to one another via a connection region, wherein the two cells come to lie in the region of the left fibrous trigone, based on the expanded and implanted state of the stent framework.

6. The heart valve prosthesis according to claim 5, characterized in that the connection region has a first and a second edge portion, wherein the two edge portions lie opposite one another in the peripheral direction, wherein a recess is formed in each edge portion, and wherein the two recesses are arranged offset relative to one another in the direction of the axis.

7. The heart valve prosthesis according to claim 1, characterized in that the first struts form two further cells of the stent framework, which are arranged adjacently in a direction of the axis and are connected to one another via a further connection region, wherein the two further cells come to lie in the region of the right fibrous trigone, based on the expanded and implanted state of the stent framework.

8. The heart valve prosthesis according to claim 7, characterized in that the further connection region has a first and a second edge portion, wherein the two edge portions lie opposite one another in the peripheral direction, wherein a recess is formed in each edge portion, and wherein the two recesses are arranged offset relative to one another in the direction of the axis.

9. The heart valve prosthesis according to claim 1, characterized in that the stent framework, in order to allow blood to flow out, defines an outflow tract, wherein the stent framework at the outflow tract has loops for anchoring the heart valve prosthesis at anterior and posterior cusps of a native mitral valve.

10. The heart valve prosthesis according to claim 9, wherein two anterior loops are provided, which are configured to anchor the heart valve prosthesis at the anterior cusp of the native mitral valve, and a posterior loop is configured to anchor the heart valve prosthesis at the posterior cusp of the native mitral valve, further wherein the posterior loop is shorter than the two anterior loops for the anterior cusp.

11. The heart valve prosthesis according to claim 1, characterized in that the stent framework has cells at an outflow tract for anchoring the heart valve prosthesis, wherein the cells are curved outwardly.

12. The heart valve prosthesis according to claim 1, characterized in that the stent framework has shortened cells on a peripheral edge of an inflow tract of the stent framework, wherein the length of the shortened cells is shorter in a direction of the axis than the length of peripheral cells that are adjacent in the peripheral direction, wherein the shortened cells are configured to come to lie in a region of an aortic peak of a native mitral valve in the expanded and implanted state of the stent framework.

13. The heart valve prosthesis according to claim 1, characterized in that the stent framework is expandable.

14. The heart valve prosthesis according to claim 1, characterized in that the heart valve prosthesis is configured to be implanted by means of a catheter.

15. The heart valve prosthesis according to claim 1, wherein a same stent framework is configured to expand to adopt two different expanded configurations, wherein a first expanded configuration comprises a circular cross-section and a second expanded configuration comprises the D-shaped cross-sectional contour, wherein the two different configurations are determined by forces acting against the stent framework.

16. The heart valve prosthesis according to claim 1, wherein the thickness of the first struts is 0.8 times the thickness of the second struts.

17. The heart valve prosthesis according to claim 1, characterized in that the stent framework is self-expanding.

18. The heart valve prosthesis according to claim 1, wherein the stent framework is not pre-set to form the D-shaped cross-sectional contour upon expansion.

* * * * *